United States Patent [19]

Mues et al.

[11] 4,427,666
[45] Jan. 24, 1984

[54] 3,5-DIHALOGENO-1,2-METHYLENEDIOXY-BENZENE ARTHROPODICIDE SYNERGIZING AGENTS

[75] Inventors: Volker Mues, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 388,566

[22] Filed: Jun. 15, 1982

Related U.S. Application Data

[63] Continuation of Ser. No. 24,747, Mar. 28, 1979, abandoned.

[30] Foreign Application Priority Data

Apr. 14, 1978 [DE] Fed. Rep. of Germany ....... 2816190

[51] Int. Cl.³ .................. A61K 31/675; A61K 31/36; C07D 317/44
[52] U.S. Cl. ..................................... 424/200; 549/434; 549/442; 549/446; 549/447; 549/436; 549/438; 424/282
[58] Field of Search ............... 549/442, 446, 447, 434, 549/436, 438; 424/282, 200

[56] References Cited

U.S. PATENT DOCUMENTS

| | | | |
|---|---|---|---|
| 2,734,908 | 2/1956 | Dengel | 549/442 |
| 2,878,265 | 3/1959 | Wachs et al. | 549/442 |
| 3,261,859 | 7/1966 | Dengel | 549/442 |
| 3,338,783 | 8/1967 | Popjak | 424/283 |
| 3,462,456 | 8/1969 | Leditschke et al. | 549/442 |
| 4,229,445 | 10/1980 | Mues et al. | 549/442 |
| 4,256,740 | 3/1981 | Mues et al. | 424/282 |

FOREIGN PATENT DOCUMENTS 2315850 1/1977 France .

OTHER PUBLICATIONS

Chemical Abstracts 12:135$^6$; 140$^6$ (1918).
Chemical Abstracts 24:2444$^6$ (1930).
Chemical Abstracts 30:2184$^2$ (1936).
Chemical Abstracts 33:546$^9$ (1939).
Chemical Abstracts 78:11425d (1973).
Chemical Abstracts 33:165 (1939).

*Primary Examiner*—Ethel G. Love
*Attorney, Agent, or Firm*—Sprung, Horn, Kramer & Woods

[57] ABSTRACT

3,5-Dihalogeno-1,2-methylenedioxybenzenes of the formula

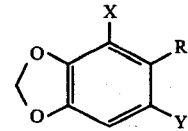

in which
  R is hydrogen, halogen, cyano or an optionally substituted alkyl, alkenyl, alkynyl, aralkyl or acyl radical, and
  X and Y each independently is halogen,
which synergize with known arthropodicides.

17 Claims, No Drawings

3,5-DIHALOGENO-1,2-METHYLENEDIOXYBENZENE ARTHROPODICIDE SYNERGIZING AGENTS

This is a continuation, of application Ser. No. 24,747, filed Mar. 28, 1979, now abandoned.

The present invention relates to and has for its objects the provision of particular new 3,5-dihalogeno-1,2-methylenedioxybenzenes which synergize with known compounds of known arthropodicidal activity, active compositions in the form of synergistic mixtures of such compounds optionally with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that the following active compounds or groups of active compounds possess pesticidal, especially insecticidal and acaricidal, properties:

(A) carbamates, for example 2-iso-propoxy-phenyl N-methyl-carbamate, 3,4,5-trimethyl-phenyl N-methyl-carbamate, 1-naphthyl N-methyl-carbamate, 2,3-dihydro-2,2-dimethyl-7-benzofuranyl N-methyl-carbamate, 2-(1,3-dioxolan-2-yl-phenyl) N-methyl-carbamate and 2,2-dimethyl-1,3-benzodioxol-4-yl N-methyl-carbamate, (B) carboxylic acid esters, for example 2,3,4,5-tetrahydrophthalimido-methyl chrysanthemate and (5-benzyl-3-furyl)methyl 2,2-dimethyl-3-(2-methyl-propenyl)-cyclopropanecarboxylate, (C) phosphoric acid esters, for example O,O-dimethyl-O-(2,2-dichlorovinyl)-phosphoric acid ester, and (D) halogenoalkanes, for example 1,1,1-trichloro-2,2-bis-(4-methoxyphenyl)-ethane and 1,1,1-trichloro-2,2-bis-(4-chlorophenyl)-ethane.

In addition, synergistic mixtures of carbamates, for example 2-iso-propoxy-phenyl N-methylcarbamate, or of phosphoric acid esters, for example O,O-diethyl-O-(2-isopropyl-4-methylpyrimidin-6-yl)-thionophosphoric acid ester, or of natural or synthetic pyrethroids, with piperonyl ethers, for example α-(2-(2-butoxy-ethoxy)-ethoxy)-4,5-methylenedioxy-2-propyl-toluene, are known (see Bull. Org. mond. Sante/Bull. Wld. Hlth Org. 1966, 35 691–708; and Schrader, G., Die Entwicklung neuer insektizider Phosphorsäureester (The Development of New Insecticidal Phosphoric Acid Esters), 1963, page 158). However, the activity of these synergistic active compound combinations is not satisfactory. Hitherto, only α-(2-(2-butoxyethoxy)-ethoxy)-4,5-methylenedioxy-2-propyl-toluene has attained some practical importance.

The present invention now provides, as new compounds, the benzodioxole derivatives of the general formula

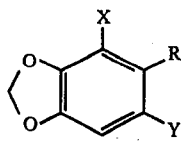

in which

R represents hydrogen, halogen, an optionally substituted alkyl, alkenyl, alkynyl, aralkyl or acyl radical or cyano and X and Y, which may be identical or different, each represent halogen.

Preferably, R represents hydrogen, chlorine, bromine, alkyl, alkenyl or alkynyl of up to 4 carbon atoms optionally substituted with chlorine, or alkanoyl or alkanoyloxy each with up to 4 carbon atoms, phenethyl, cyanor or a radical of the formula

wherein $R^{16}$ represents hydrogen or methyl and $R^{17}$ represents hydrogen, straight-chain or branched alkyl with 1 to 5 (especially 1 to 3) carbon atoms, allyl, propargyl or benzyl, and X and Y represent fluorine, chlorine, bromine or iodine.

The invention also provides a process for the preparation of a compound of the formula (I), in which (a) a 1,2-dihydroxybenzene of the general formula

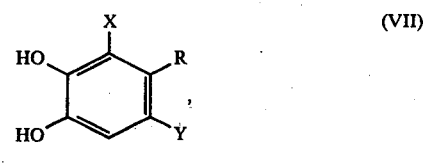

in which

R, X and Y have the above-mentioned meanings, is reacted with a dihalogenomethane of the general formula

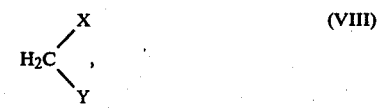

wherein

X and Y have the above-mentioned meanings, in the presence of an acid acceptor and, if appropriate, in the presence of a diluent, or (b) a benzodioxole derivative of the general formula

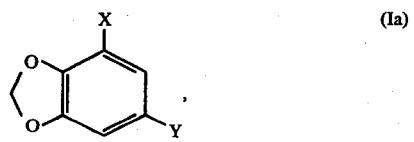

in which

X and Y have the above-mentioned meanings, is reacted with a halogenating agent or with formaldehyde/HCl to give a compound of the formula (I), in which X and Y have the above-mentioned meanings and R represents halogen or $CH_2Cl$, or (c) a benzodioxole derivative of the general formula

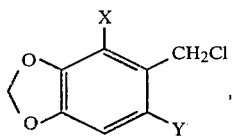

in which
X and Y have the above-mentioned meanings, is converted by catalytic hydrogenation into a compound of the formula (I)
in which
R represents methyl, or is converted by reaction with a compound which contains the acetate ion or cyanide ion, for example with sodium acetate or sodium cyanide, into a compound of the formula (I),
in which
R represents acetoxymethyl or cyanomethyl, or is converted, by reaction with hexamethylenetetramine, into a compound of the formula (I),
in which
R represents formyl,
or
(d) a benzodioxole derivative of the general formula

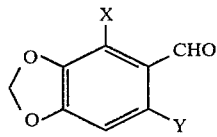

in which
X and Y have the above-mentioned meanings, is converted to the corresponding oxime by means of hydroxylamine, and the oxime is treated with a dehydrating agent to produce a compound of the formula (I),
in which
R represents cyano,
or
(e) a benzodioxole derivative of the general formula

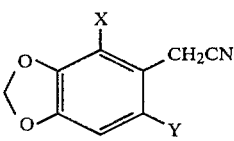

in which
X and Y have the above-mentioned meanings, is reacted with a halogenoalkane, halogenoalkene or halogenoalkyne to give a compound of the general formula

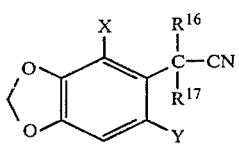

in which
X, Y, $R^{16}$ and $R^{17}$ have the above-mentioned meanings.

The invention also provides an arthropodicidal composition containing as active ingredients (1) at least one compound of the formula (I) and (2) at least one compound selected from (A) carbamates, (B) carboxylic acid esters (including the natural and synthetic pyrethroids), (C) phosphoric acid esters and (D) halogenoalkanes, alone or in admixture with a diluent or carrier.

The invention also provides a method of combating arthropods, especially insects or acarids, which comprises applying to the arthropods, or to a habitat thereof, a composition according to the invention.

The synergistic action of the compounds of the general formula (I) manifests itself preferentially with compounds of certain preferred classes.

Preferred carbamates (A) are those of the general formula

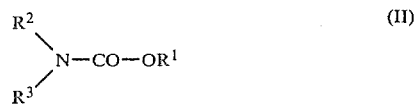

in which
$R^1$ represents aryl, a heterocyclic ring or an oxime radical,
$R^2$ represents hydrogen or an alkyl radical with 1 to 4 carbon atoms and
$R^3$ represents alkyl, alkylcarbonyl with 1 to 6 carbon atoms in the alkyl radical, which optionally can also be substituted by hydroxyl or methylthio, or the radical -S-Z,
wherein
Z represents an optionally halogen-substituted aliphatic radical with 1 to 4 carbon atoms (especially $CCl_3$ and $CF_3$), an optionally substituted aryl radical (especially phenyl) (preferred substituents being nitrile, halogen, especially chlorine, methyl, trihalogenomethyl, trifluoromethylmercapto or nitro), methoxycarbonyl or the radical

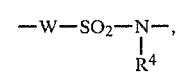

wherein
W represents alkyl, halogenoalkyl, alkylamino, dialkylamino or an optionally substituted aryl radical (preferred substituents being halogen, trihalogenomethyl, nitrile, methyl or nitro).

Particularly preferred carbamates of the formula (II) are those
wherein
$R^1$ represents phenyl or naphthyl, which are optionally substituted by alkyl, alkenyl, alkoxy, alkylmercapto or alkylthioalkyl, in each case with 1 to 6 carbon atoms, dialkylamino and dialkenylamino, with up to 3 carbon atoms per alkyl or alkenyl part, halogen, especially chlorine, dioxolanyl or the $-N=CH-N(C_{1-4}-alkyl)_2$ radical, or
wherein
$R^1$ represents 2,3-dihydrobenzofuranyl, benzodioxole, benzothienyl, pyrimidinyl or pyrazolyl, which are optionally substituted by alkyl with 1 to 4 carbon atoms (especially methyl) or by dialkylamino with 1 to 4 carbon atoms per alkyl part, or
wherein
$R^1$ represents a radical of the general formula

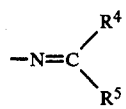

in which
R⁴ and R⁵, which may be identical or different, each represent alkyl, cycloalkyl, alkenyl, alkynyl, alkoxy, alkylmercapto, alkoxycarbonyl, carbamoyl or alkylmercaptoalkyl, in each case with up to 6 carbon atoms, nitrile, aryl (especially phenyl), or R⁴ and R⁵ conjointly represent a dioxolanyl or dithioalanyl radical which is optionally substituted by $C_{1-4}$-alkyl.

The following carbamates of the formula (II) may be mentioned specifically: 2-methylphenyl, 2-ethylphenyl, 2-n-propylphenyl, 2-methoxyphenyl, 2-ethoxyphenyl, 2-isopropoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-(1,3-dioxolan-2-yl-phenyl) and 2,2-dimethyl-1,3-benzodioxol-4-yl N-methyl-carbamate and the corresponding N-methyl-N-acetyl-, N-methyl-N-trifluoromethylthio-, N-methyl-N-dichloromonofluoromethylthio- and N-methyl-N-dimethylaminothio-carbamates.

Preferred carboxylic acid esters (B) are those of the general formula

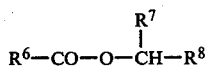

in which
R⁶ represents alkyl, aralkyl, aryl or cycloalkyl, which can optionally be substituted,
R⁷ represents hydrogen, alkyl, halogenoalkyl, alkenyl, alkynyl or nitrile and
R⁸ represents aryl or a heterocyclic ring, or conjointly with R⁷ forms an optionally substituted cyclopentenone ring.

Particularly preferred carboxylic acid esters (III) are those
in which
R⁶ represents alkyl with 1 to 6 carbon atoms, which is optionally substituted by optionally halogen-substituted phenyl, or represents cyclopropyl, which is optionally substituted by alkyl, alkenyl, halogenoalkyl or halogenoalkenyl, each with up to 6 carbon atoms, or represents phenyl, which is optionally substituted by halogen,
R⁷ represents hydrogen, alkyl with 1 to 6 carbon atoms, halogenoalkyl with 1 to 4 carbon atoms and up to 3 halogen atoms, nitrile or ethynyl,
R⁸ represents phenyl which is optionally substituted by $C_{1-4}$-alkyl, halogen, especially fluorine or chlorine, or optionally halogen-substituted or methyl-substituted phenoxy or optionally substituted benzyl, or represents furanyl, tetrahydrophthalimido, or benzodioxole, which are optionally substituted by halogen, especially chlorine, alkyl or alkenyl with up to 4 carbon atoms, or benzyl, or, together with R⁷ and the CH moiety, represents cyclopentenone which is optionally substituted by $C_{1-4}$-alkyl, furfuryl or $C_{1-5}$-alkenyl.

The following may be mentioned specifically: 1-(3,4-dichlorophenyl)-2,2,2-trichloroethyl acetate, 2,3,4,5-tetrahydrophthalimidomethyl chrysanthemate and (5-benzyl-3-furyl)-methyl 2,2-dimethyl-3-(2-methylpropenyl)-cyclopropanecarboxylate. In addition, the naturally occurring pyrethroids are also particularly preferred.

Preferred phosphoric acid esters (C) are those of the general formula

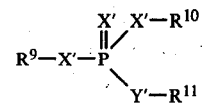

in which
each X' independently of the others represents O or S,
Y' represents O, S, —NH— or a direct bond between the central P atom and R¹¹, and
R⁹ and R¹⁰, which may be identical or different, each represent alkyl or aryl, and
R¹¹ represents alkyl, aryl, heteroaryl, aralkyl, alkenyl, dioxanyl or an oxime radical, or a radical identical to that to which it is bonded.

Particularly preferred phosphoric acid esters (IV) are those
in which
R⁹ and R¹⁰, which may be identical or different, each represent $C_{1-4}$-alkyl or phenyl, and
R¹¹ represents alkyl with 1 to 4 carbon atoms, which is optionally substituted by halogen, hydroxyl, nitrile, optionally halogen-substituted phenyl, amidocarbonyl, $C_{1-4}$-alkylamidocarbonyl, sulphonyl-$C_{1-4}$-alkyl, sulphoxy-$C_{1-4}$-alkyl, carbonyl-$C_{1-4}$-alkyl, $C_{1-4}$-alkoxy, $C_{1-4}$-alkylmercapto or $C_{1-4}$-alkoxy-carbonyl, or represents alkenyl with up to 4 carbon atoms, which is optionally substituted by halogen, optionally halogen-substituted phenyl or alkoxy-carbonyl, or represents an oxime radical of the general formula

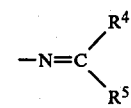

wherein
R⁴ and R⁵ have the above-mentioned meanings, but in particular represent cyano or phenyl, or
R¹¹ represents dioxanyl which is substituted by a radical identical to that to which R¹¹ is bonded, or R¹¹ represents a radical identical to that to which it is bonded, or R¹¹ represents phenyl which is optionally substituted by methyl, nitro, nitrile, halogen or methylthio, or, particularly preferentially, R¹¹ represents an optionally $C_{1-4}$-alkyl-substituted or halogen-substituted heteroaromatic, such as pyridine, quinoline, quinoxaline, pyrimidine, diazinone or benzo-1,2,4-triazine.

The following may be mentioned specifically: O,O-dimethyl- and O,O-diethyl-O-(2,2-dichloro- or 2,2-dibromo-vinyl)-phosphoric acid ester, O,O-diethyl-O-(4-nitro-phenyl)-thionophosphoric acid ester, O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthio-phenyl)-thionophosphoric acid ester, O,O-dimethyl-S-(4-oxo-1,2,3-benzotriazin-3-yl-methyl)-thionothiolphosphoric acid ester, O-methyl-O-(2-iso-propyl-6-methoxy-pyrimidin-4-yl)-thionomethanephosphonic acid ester, O,O-diethyl-O-(2-iso-propyl-6-methyl-pyrimidin-4-yl)-thionophosphoric acid ester, O,O-diethyl-O-(3-chloro-4-methylcoumarin-7-yl)-thionophosphoric acid ester, O,O-dimethyl-2,2,2-trichloro-1-hydroxy-ethane-phosphonic acid ester and O,O-dimethyl-S-(methylcarbamoylmethyl)-thionophosphoric acid ester.

Preferred halogenoalkanes (D) are those of the general formula

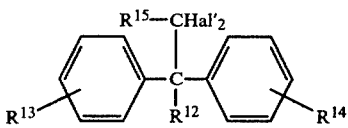

in which
Hal' represents chlorine or bromine and
$R^{12}$ represents hydrogen or hydroxyl,
$R^{13}$ and $R^{14}$, which may be identical or different, each represent halogen, alkyl or alkoxy and
$R^{15}$ represents hydrogen or halogen.

Particularly preferred halogenoalkanes (V) are those in which
$R^{12}$ represents hydrogen or hydroxyl,
$R^{13}$ and $R^{14}$ are identical and represent halogen, alkyl with 1 to 4 carbon atoms or alkoxy with 1 to 4 carbon atoms and
$R^{15}$ represents halogen.

The following may be mentioned specifically: 1,1,1-trichloro-2,2,-bis(4-chloro- or 4-methoxy-phenyl)-ethane, 1,1,1-trichloro-2-hydroxy-2,2-bis(4-chlorophenyl)-ethane and 1,1-dichloro-2,2-bis(4-ethylphenyl)-ethane.

Surprisingly, the insecticidal and/or acaricidal action of the active compound combinations according to the invention is substantially greater than the action of the individual components and greater than the sum of the actions of the individual components. Furthermore, it is substantially greater than the action of the previously known active compound combination of 2-iso-propoxyphenyl-N-methyl-carbamate and piperonyl butoxide. In addition, the benzodioxole derivatives which can be used according to the invention exhibit an excellent synergistic activity, not only with one class of active compounds, but with active compounds from a great variety of groups of chemical compounds.

Accordingly, the benzodioxole derivatives according to the invention, and the synergistic mixtures in which they are present, represent a valuable enrichment of the art.

The following may be mentioned as specific examples of the benzodioxoles of the formula (I): 3,5-difluoro-, 3,5-dichloro-, 3,5-dibromo-, 3,5-diiodo-, 3-fluoro-5-chloro-, 3-fluoro-5-bromo-, 3,-fluoro-5-iodo-, 3-chloro-5-fluoro-, 3-chloro-5-bromo-, 3-chloro-5-iodo-, 3-bromo-5-fluoro-, 3-bromo-5-chloro-, 3-bromo-5-iodo-, 3-iodo-5-fluoro-, 3-iodo-5-chloro- and 3-iodo-5-bromo-1,2-methylenedioxybenzene, 3,5-difluoro-4-bromo-, 3,5-dichloro-4-bromo-, 3,4,5-tribromo-, 3,5-diiodo-4-bromo-, 3-fluoro-5-chloro-4-bromo-, 3-fluoro-4,5-dibromo-, 3-fluoro-5-iodo-4-bromo-, 3-chloro-5-fluoro-4-bromo-, 3-chloro-4,5-dibromo-, 3-chloro-5-iodo-4-bromo-, 3,4-dibromo-5-fluoro-, 3,4-dibromo-5-chloro-, 3,4-dibromo-5-iodo-, 3-iodo-5-fluoro-4-bromo-, 3-iodo-5-chloro-4-bromo- and 3-iodo-4,5-dibromo-1,2-methylenedioxybenzene, 3,5-difluoro-4-chloro-, 3,4,5-trichloro-, 3,5-dibromo-4-chloro-, 3,5-diiodo-4-chloro-, 3-fluoro-4,5-dichloro-, 3-fluoro-5-bromo-4-chloro-, 3-fluoro-5-iodo-4-chloro-, 3,4-dichloro-5-fluoro-, 3,4-dichloro-5-bromo-, 3,4-dichloro-5-iodo-, 3-bromo-5-fluoro-4-chloro-, 3-bromo-4,5-dichloro-, 3-bromo-5-iodo-4-chloro-, 3-iodo-5-fluoro-4-chloro-, 3-iodo-4,5-dichloro- and 3-iodo-5-bromo-4-chloro-1,2-methylenedioxybenzene, and also 3,5-difluoro-, 3,5-dichloro-, 3,5-dibromo-, 3,5-diiodo-, 3-fluoro-5-chloro-, 3-fluoro-5-bromo-, 3-fluoro-5-iodo-, 3-chloro-5-fluoro-, 3-chloro-5-bromo-, 3-chloro-5-iodo-, 3-bromo-5-fluoro-, 3-bromo-5-chloro-, 3-bromo-5-iodo-, 3-iodo-5-fluoro-, 3-iodo-5-chloro-, 3-iodo-5-bromo-4-methyl-, -4-chloromethyl-, -4-formyl-, -4-acetoxymethyl-, -4-cyano-, -4-cyanomethyl-, -4-(1-cyano-ethyl)-, -4-(1-cyano-n-propyl)-, -4-(1-cyano-iso-propyl)-, -4-(1-cyano-n-butyl)-, -4-(1-cyano-iso-butyl)-, -4-(1-cyano-sec.-butyl)-, -4-(1-cyano-but-3-enyl)-, -4-(1-cyano-but-3-ynyl)- and -4-(1-cyano-2-phenyl-ethyl)-1,2-methylenedioxybenzene.

If 3,4-dichloro-5-bromo-1,2-dihydrobenzene and methylene chloride are used as starting compounds in process variant (a), the equation can be represented by the following equation:

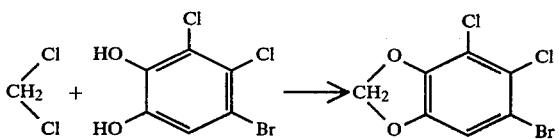

Starting from benzodioxoles of the formula (I), in which R represents hydrogen (formula (Ia)), and which can be prepared in accordance with the method explained above, benzodioxole derivatives according to the invention can be prepared in accordance with the following sets of equations:

Reaction with halogenating agents, such as sulphuryl chloride or bromine, gives compounds of the formula (Ib), wherein Hal represents chlorine or bromine. Reaction with formaldehyde/hydrochloric acid gives the chloromethylbenzodioxoles of the formula (Ic):

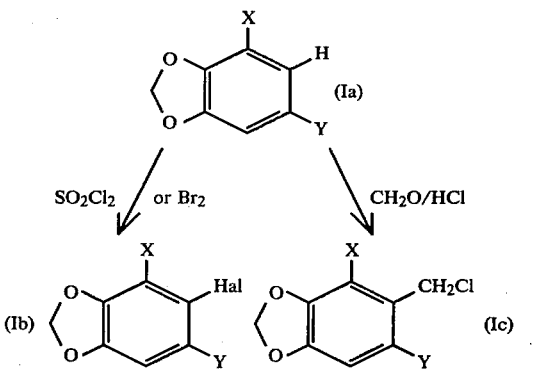

The chloromethyl-benzodioxoles (Ic) can be employed for the preparation of the other active compounds according to the invention. They react with hydrogen, in the presence of a transition metal catalyst, to form 4-methyl-benzodioxoles (Id), react with acetate to form 4-acetoxymethyl-benzodioxoles (Ie), and react with cyanide to form 4-cyanomethyl-benzodioxoles (If):

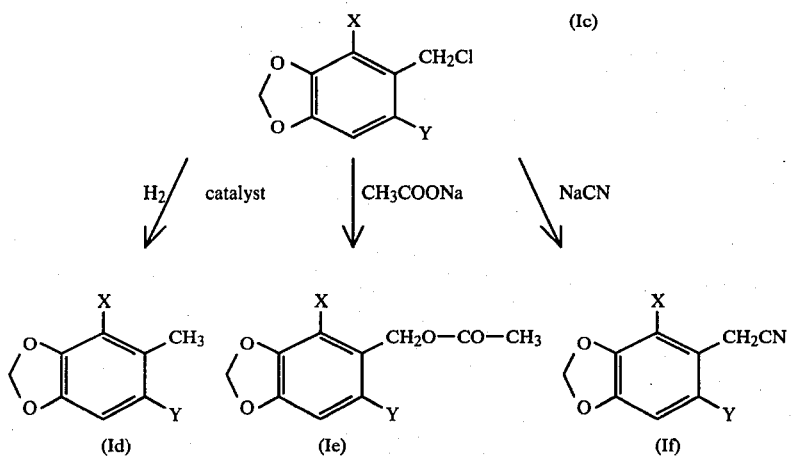

Reaction of the chloromethyl-benzodioxoles (Ic) with hexamethylenetetramine gives formyl-benzodioxoles (Ig). These can be converted into oximes (Ih) by reaction with hydroxylamine, and the oximes can be further converted into nitriles (Ik) by means of dehydrating agents, for example acetic anhydride:

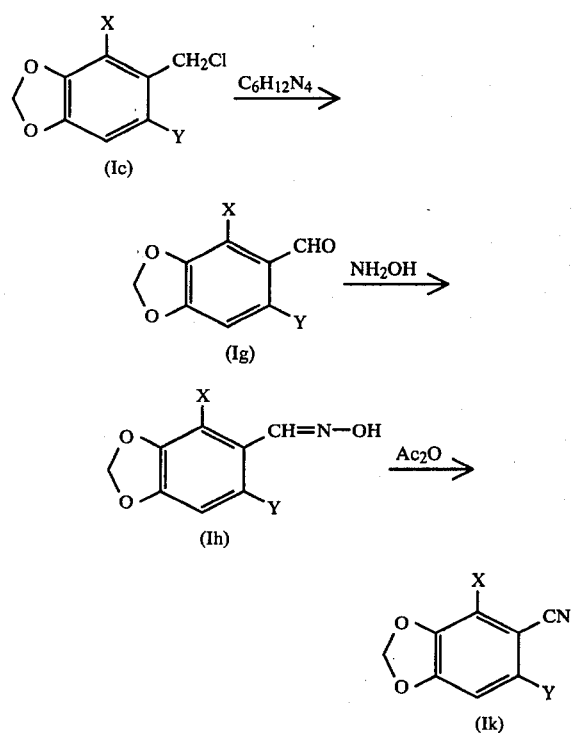

Reaction of the cyanomethyl-benzodioxoles (If) with the corresponding halogenoalkanes, -alkenes or -alkynes permits the preparation of the cyanoalkyl-, cyanoalkenyl- or cyanoalkynyl-benzodioxoles, which are further compounds according to the invention (compare DT-OS (German Published Specification) 2,215,496; Pure Appl. Chem. 43 (1975), page 439; Org. Syn. 55 (1976), page 91):

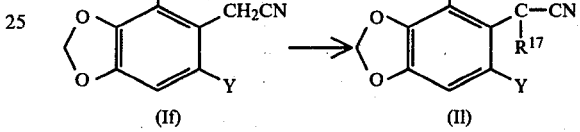

The 1,2-dihydroxybenzenes (VII), to be used as intermediates for the preparation of the benzodioxoles (I) according to the invention, can be prepared from the partially known 2-hydroxy-benzaldehyde derivatives, such as, for example, 3,5-dichlorosalicylaldehyde, by reaction with hydrogen peroxide in accordance with the so-called Dakin oxidation (see Am. Chem. J. 42, 488; British Patent Specification No. 794,885; Biochem. Journal 59 (1955), pages 410–415; Chem. Abstr. 49 (1955), 7675h) of the following equation:

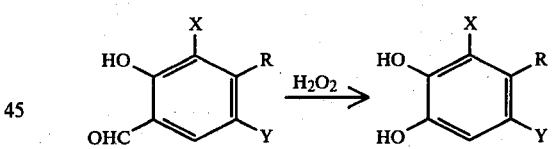

As already mentioned, the new active compound combinations comprising the benzodioxole derivatives according to the invention, of the formula (I), together with carbamates, carboxylic acid esters, phosphoric acid esters and/or halogenoalkanes, exhibit an excellent increase in action compared to the individual active compounds and compared to the sum of their actions.

The weight ratios of the groups of active compounds can vary within relatively wide ranges. In general, the benzodioxole derivatives—component (1)—are employed together with the remaining active compounds—component (2)—in a ratio of about 0.1:10 to 10:0.1. However, ratios, in the mixture of about 0.5:1.0 to 3.0:1.0 have proved particularly suitable.

These active compound combinations not only have a rapid knock-down action, but also, over a long period, cause the destruction of arthropod pests, especially insects and arachnids, which are encountered in agriculture, in forestry, in the protection of stored products and of materials, and in the hygiene field. They are active against normally sensitive and resistant species and against all of some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psyll-oides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaconis* and Vespa spp.;

from the order of the Diptera, for example Aedes spp., Anopheles spp., Cu spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane, or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

Furthermore, the invention provides crops protected from damage by arthropods by being grown in areas in which immediately prior to and/or during the time of the growing a composition of the present invention was applied.

It will be seen that the usual methods of providing a harvested crop may be improved by the present invention.

PREPARATIVE EXAMPLES

Example 1

(a) Preparation of benzodioxoles of the formula (I)

4.4 moles of potassium carbonate were added, while stirring, to a solution of 2.0 moles of pyrocatechol derivative (VII) in 1,500 ml of dimethylformamide, the suspension was warmed to 60°–70° C. and 2.2 moles of chlorobromomethane were added dropwise. In the course thereof, the temperature rose and was kept at 95° C. by cooling. When the reaction had subsided, the mixture was stirred for a further 5 hours at 100° C. and was filtered, and the solvent was distilled from the filtrate in vacuo. The residue was taken up in toluene and the solution was washed with water, with dilute sodium hydroxide solution and again with water and was dried over sodium sulphate. The solvent was distilled off and the residue was recrystallized.

Using this procedure it was possible to prepare, for example, the following compounds of the formula (Ia):

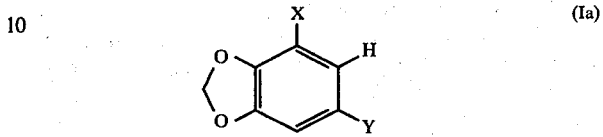

| Compound No. | X | Y | Yield (% of theory) | Melting point (°C.) |
|---|---|---|---|---|
| 1 | Cl | Cl | 72 | 55 |
| 2 | Cl | Br | 40 | 68 |
| 3 | Br | Cl | 43 | 67 |
| 4 | Br | Br | 42 | 81 |

(b) Chlorination of benzodioxoles of the formula (Ia)

0.11 mole of sulphuryl chloride was added dropwise, at room temperature, to 0.1 mole of 3,5-dihalogeno-1,2-methylenedioxybenzene (Ia) dissolved in 100 ml of methylene chloride, and the mixture was heated to the boil for 2 hours, while stirring. When it had cooled, it was washed with water, with sodium bicarbonate solution and again with water and was dried over calcium chloride; the solvent was distilled off in vacuo and the residue was recrystallized.

(c) Bromination of benzodioxoles of the formula (Ia)

A solution of 0.105 mole of bromine in 10 ml of glacial acetic acid was added dropwise, at room temperature, to a solution of 0.1 mole of 3,5-dihalogeno-1,2-methylenedioxybenzene (Ia) in 150 ml of glacial acetic acid and the mixture was stirred for 4 hours at room temperature. The reaction mixture was then poured into water and was extracted with methylene chloride, and the organic phase was washed with water and dried over calcium chloride. After distilling off the solvent in vacuo, the residue was recrystallized.

Following the procedure (b) or (c) it was possible to prepare, for example, the following 3,4,5-trihalogeno-1,2-methylenedioxybenzodioxoles of the formula (Ib):

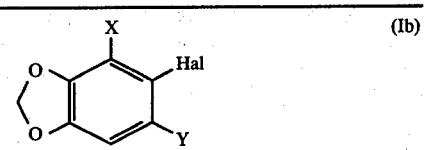

| Compound No. | X | Y | Hal | Yield (% of theory) | Melting point (°C.) |
|---|---|---|---|---|---|
| 5 | Cl | Cl | Cl | 44 | 110 |
| 6 | Br | Br | Cl | 48 | 122 |
| 7 | Br | Cl | Cl | 35 | 105 |
| 8 | Cl | Cl | Br | 89 | 86 |

Example 2

(a) Chloromethylation of benzodioxoles of the formula (Ia)

0.5 mole of 3,5-dihalogeno-1,2-methylenedioxybenzene (Ia) was stirred with 70 ml of formalin in 300 ml of concentrated hydrochloric acid for 24 hours at 50°–60° C. After cooling, the reaction mixture was extracted with toluene and the organic phase was washed neutral with water and dried over sodium sulphate. The solvent was stripped off in vacuo and the residue was purified by vacuum distillation.

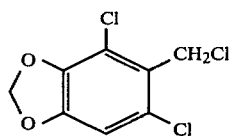
(9)

3,5-Dichloro-4-chloromethyl-1,2-methylenedioxybenzene, of boiling point 140° C./2 mm Hg and melting point 64° C., in a yield of 74% of theory.

(b) Preparation of benzodioxoles of the formula (Id)

0.5 mole of 3,5-dihalogeno-4-chloromethyl-1,2-methylenedioxybenzene (Ic) was dissolved in 1,000 ml of toluene, 1.0 mole of triethylamine was added and after adding 10 g of Raney nickel the mixture was hydrogenated at 80° C. under 65 bars of hydrogen. After the mixture had cooled, the catalyst and the precipitated triethylammonium chloride were filtered off and the organic phase was washed and then dried over sodium sulphate. The solvent was stripped off in vacuo and the residue was purified by vacuum distillation.

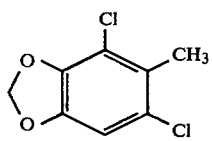
(10)

3,5-Dichloro-4-methyl-1,2-methylenedioxybenzene, of boiling point 98° C./2 mm Hg and melting point 80° C., in a yield of 85% of theory.

(c) Preparation of benzodioxoles of the formula (Ie)

0.5 mole of 3,5-dihalogeno-4-chloromethyl-methylenedioxybenzene (Ic) was dissolved in 500 ml of glacial acetic acid and 0.6 mol of anhydrous sodium acetate was added. The mixture was heated to the boil under reflux overnight, while stirring. After it had cooled, the reaction mixture was poured onto ice water. The product which thereupon precipitated was washed with water and then with petroleum ether, and was dried.

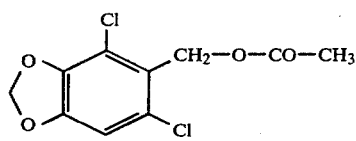
(11)

3,5-Dichloro-4-acetoxymethyl-1,2-methylenedioxybenzene, of melting point 64° C., in a yield of 98% of theory.

Example 3

(a) Preparation of benzodioxoles of the formula (If)

A solution of 5 g of potassium iodide in 20 ml of water was added to a solution of 1.05 moles of sodium cyanide in 500 ml of dimethylformamide and 1.0 mol of 3,5-dihalogeno-4-chloromethyl-1,2-methylenedioxybenzene (Ic) was metered in, at an internal temperature of 60° C., at a rate such that the slightly exothermic reaction took place at 60° C. After stirring for 5 hours at room temperature, the mixture was poured into 3 liters of water and was extracted with toluene, the organic phase was washed neutral and dried over sodium sulphate, the solution was clarified with active charcoal/Tonsil, and the solvent was stripped off in vacuo. The crystalline residue was suspended in ether/petroleum ether (1:1), filtered off and dried.

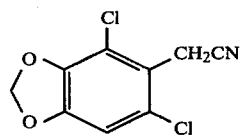
(12)

3,5-Dichloro-4-cyanomethyl-1,2-methylenedioxybenzene, of melting point 115° C., in a yield of 65% of theory.

(b) Preparation of benzodioxoles of the formula (II)

1.0 mole of 3,5-dihalogeno-4-cyanomethyl-1,2-methylenedioxybenzene (If) was added to a suspension of 1.1 moles of potassium tert.-butylate in 1.5 liters of toluene at 25°–30° C., with slight cooling. The mixture was stirred for 30 minutes at 40°–50° C., and 1.1 moles of halogenoalkane, halogenoalkene or halogenoalkyne were then added dropwise at 50° C. After stirring for 3 hours under reflux, the mixture was cooled, water was added and the organic phase was washed until neutral and dried over sodium sulphate. The solvent was stripped off in vacuo and the residue was purified by distillation or recrystallization.

The following compounds were prepared analogously:

(II')

| Compound No. | Alk | Yield (% of theory) | Melting point (°C.); boiling point (°C./mm Hg) |
|---|---|---|---|
| 13 | CH$_3$ | 70 | 103 |
| 14 | C$_2$H$_5$ | 73 | 160/2 |
| 15 | C$_3$H$_7$—iso | 42 | 166/2 |
| 16 | CH$_2$=CH$_2$—CH$_2$— | 65 | 168/2 |

The following was obtained analogously to Example 1 (b):

| Compound No. | X | Y | R |
|---|---|---|---|
| 17 | Cl | Br | Cl |

The activity of the compounds of this invention is illustrated by the following example:

Example 4

$LT_{100}$ test

Test insects: *Musca domestica*, Weymanns strain (resistant to carbamates and phosphoric acid esters)

Solvent: Acetone

Solutions were prepared from the active compounds, synergistic agents and mixtures of active compounds and synergistic agents, and 2.5 ml of the solutions were pipetted onto filter paper discs of 9.5 cm diameter in Petri dishes. The filter paper adsorbed the solutions. The Petri dishes were left standing open until the solvent had completely evaporated. 25 test insects were then introduced into the Petri dishes, and the dishes were covered with a glass lid.

The condition of the test insects was checked continuously for up to 6 hours. The time required for a 100% knock-down action was determined. If the $LT_{100}$ was not reached after 6 hours, the percentage of the test insects which had been knocked down was determined.

The concentrations of the active compounds, synergistic agents and mixtures, and their actions can be seen from the table which follows.

TABLE

LT 100 test with *Musca domestica* (Weymanns strain), resistant to phosphoric acid esters

| Active compounds ( ) identifying letter | or | Synergistic agents ( ) Compound No. | Concentration in % | LT 100 or % after 360 minutes |
|---|---|---|---|---|
|  (A) | | | 1.0 | 360' = 0% |
| 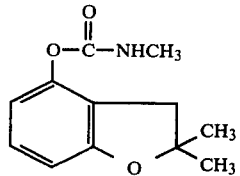 (B) | | | 1.0 | 360' = 0% |
| 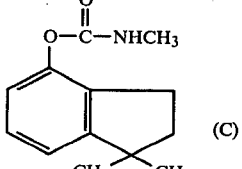 (C) | | | 1.0 | 360' = 0% |
| 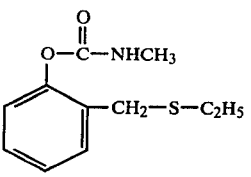 (D) | | | 1.0 | 360' = 0% |
| 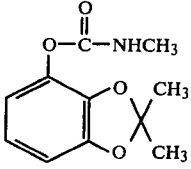 (E) | | | 1.0 | 360' = 0% |

TABLE-continued

| Active compounds ( ) identifying letter or | LT 100 test with *Musca domestica* (Weymanns strain), resistant to phosphoric acid esters | | |
|---|---|---|---|
| | Synergistic agents ( ) Compound No. | Concentration in % | LT 100 or % after 360 minutes |
| (F) carbamate structure | | 1.0 | 360' = 0% |
| (G) carbamate structure | | 1.0 | 360' = 15% |
| (H) CH₃—HN—C(=O)—O—N=C(CH₃)—S—CH₃ | | 0.04 | 360' = 0% |
| Pyrethrins in the form of a 25% strength extract (K) | | 0.04 | 360' = 60% |
| (L) structure | | 0.008 | 360' = 40% |
| (M) structure | | 0.04 | 360' = 45% |
| (N) structure | | 0.008 | 360' = 95% |
| (O) structure | | 0.04 | 0.04 = 90' |
| (P) structure | | 1.0 | 360' = 10% |

TABLE-continued

| Active compounds ( ) identifying letter | or | Synergistic agents ( ) Compound No. | Concentration in % | LT 100 or % after 360 minutes |
|---|---|---|---|---|
| (Q) Hexachlorocyclohexane (H isomer) | | | 1.0 | 360' |
| (R) (4-Cl-C$_6$H$_4$)$_2$CH-CCl$_3$ | | | 1.0 | 360' = 5% |
| (S) (4-CH$_3$O-C$_6$H$_4$)$_2$CH-CCl$_3$ | | | 1.0 | 360' = 20% |
| (T) 3-chloro-4-methyl-7-[(diethoxyphosphinothioyl)oxy]-2H-chromen-2-one | | | 1.0 | 360' = 0% |
| (U) CCl$_2$=CH-O-P(O)(OCH$_3$)$_2$ | | | 0.008 | 360' = 90% |
| (V) CH$_3$HN-C(O)-CH$_2$-S-P(O)(OCH$_3$)$_2$ | | | 0.04 | 360' = 25% |
| (W) benzotriazinone-CH$_2$-S-P(S)(OCH$_3$)$_2$ | | | 1.0 | 360' = 65% |
| (X) CCl$_3$-CH(OH)-P(O)(OCH$_3$)$_2$ | | | 1.0 | 360' = 45% |
| (Y) 4-(CH$_3$S)-3-(CH$_3$)-C$_6$H$_3$-O-P(S)(OCH$_3$)$_2$ | | | 0.2 | 360' = 10% |
| (Z) C$_2$H$_5$-O-C(O)-CH(S-P(S)(OCH$_3$)$_2$)-CH$_2$-C(O)-O-C$_2$H$_5$ | | | 1.0 | 360' = 65% |

LT 100 test with *Musca domestica* (Weymanns strain), resistant to phosphoric acid esters

| Active compounds ( ) identifying letter | or | Synergistic agents ( ) Compound No. | Concentration in % | LT 100 or % after 360 minutes |
|---|---|---|---|---|
| | | 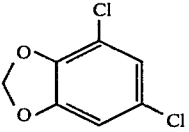 (1) | 0.2 | 360' = 0% |
| | | 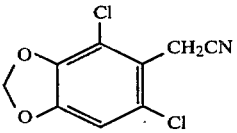 (12) | 1.0 | 360' = 0% |
| | | 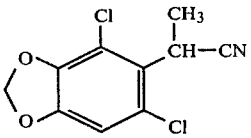 (13) | 1.0 | 360' = 0% |
| | | 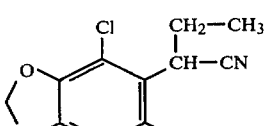 (14) | 1.0 | 360' = 0% |
| | | 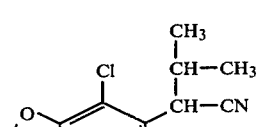 (15) | 1.0 | 360' = 0% |
| | | 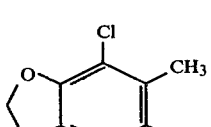 (10) | 1.0 | 360' = 0% |
| | | 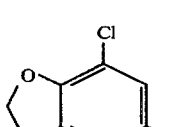 (2) | 0.2 | 360' = 0% |
| | | 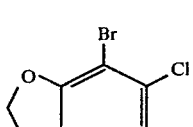 (6) | 1.0 | 360' = 0% |

TABLE-continued

LT 100 test with *Musca domestica* (Weymanns strain), resistant to phosphoric acid esters

| Active compounds ( ) identifying letter | or | Synergistic agents ( ) Compound No. | Concentration in % | | | LT 100 or % after 360 minutes |
|---|---|---|---|---|---|---|
| | | (7) [structure: benzodioxole with Br, Cl, Cl substituents] | 1.0 | | | 360' = 0% |
| | | (17) [structure: benzodioxole with Cl, Cl, Br substituents] | 1.0 | | | 360' = 0% |
| | | Comparison agent: | | | | |
| | | Piperonylbutoxide | 1.0 | | | 360' = 0% |
| A | + | Piperonylbutoxide | 0.04 | + | 0.04 | 360' = 0% |
| A | + | 1 | 0.008 | + | 0.008 | 150' |
| A | + | 12 | 0.04 | + | 0.04 | 360' = 95% |
| A | + | 13 | 0.04 | + | 0.04 | 360' |
| A | + | 14 | 0.04 | + | 0.04 | 360' |
| A | + | 15 | 0.04 | + | 0.04 | 210' |
| A | + | 10 | 0.008 | + | 0.008 | 360' |
| A | + | 2 | 0.04 | + | 0.04 | 105' |
| A | + | 6 | 0.008 | + | 0.008 | 360' = 85% |
| A | + | 7 | 0.04 | + | 0.04 | 180' |
| A | + | 17 | 0.04 | + | 0.04 | 360' = 75% |
| B | + | Piperonylbutoxide | 0.2 | + | 0.2 | 360' = 95% |
| B | + | 1 | 0.008 | + | 0.008 | 210' |
| B | + | 13 | 0.04 | + | 0.04 | 240' |
| B | + | 14 | 0.2 | + | 0.2 | 240' |
| B | + | 15 | 0.04 | + | 0.04 | 210' |
| B | + | 10 | 0.008 | + | 0.008 | 210' |
| B | + | 2 | 0.008 | + | 0.008 | 150' |
| C | + | Piperonylbutoxide | 1.0 | + | 1.0 | 360' = 0% |
| C | + | 1 | 1.0 | + | 1.0 | 150' |
| C | + | 13 | 1.0 | + | 1.0 | 360' = 80% |
| C | + | 14 | 1.0 | + | 1.0 | 360' = 95% |
| C | + | 15 | 1.0 | + | 1.0 | 360' |
| C | + | 10 | 0.2 | + | 0.2 | 360' = 95% |
| C | + | 2 | 0.2 | + | 0.2 | 360' |
| D | + | Piperonylbutoxide | 0.2 | + | 0.2 | 360' = 0% |
| D | + | 1 | 0.2 | + | 0.2 | 150' |
| D | + | 14 | 0.2 | + | 0.2 | 360' = 70% |
| D | + | 15 | 0.2 | + | 0.2 | 360' = 80% |
| D | + | 10 | 0.2 | + | 0.2 | 240' |
| D | + | 2 | 0.2 | + | 0.2 | 120' |
| E | + | Piperonylbutoxide | 0.2 | + | 0.2 | 360' = 10% |
| E | + | 1 | 0.008 | + | 0.008 | 360' = 95% |
| E | + | 12 | 0.04 | + | 0.04 | 240' |
| E | + | 13 | 0.04 | + | 0.04 | 180' |
| E | + | 14 | 0.04 | + | 0.04 | 180' |
| E | + | 15 | 0.04 | + | 0.04 | 150' |
| E | + | 10 | 0.008 | + | 0.008 | 210' |
| E | + | 2 | 0.008 | + | 0.008 | 180' |
| F | + | Piperonylbutoxide | 0.2 | + | 0.2 | 360' = 5% |
| F | + | 1 | 0.2 | + | 0.2 | 150' |
| F | + | 12 | 0.2 | + | 0.2 | 360' = 75% |
| F | + | 13 | 0.04 | + | 0.04 | 360' = 70% |
| F | + | 10 | 0.04 | + | 0.04 | 360' = 80% |
| F | + | 2 | 0.04 | + | 0.04 | 360' = 90% |
| G | + | Piperonylbutoxide | 0.04 | + | 0.04 | 360' = 15% |
| G | + | 1 | 0.008 | + | 0.008 | 360' |
| G | + | 10 | 0.008 | + | 0.008 | 360' = 90% |
| G | + | 2 | 0.04 | + | 0.04 | 180' |
| H | + | Piperonylbutoxide | 0.2 | + | 0.2 | 360' = 95% |
| H | + | 1 | 0.04 | + | 0.04 | 360' |
| H | + | 13 | 0.2 | + | 0.2 | 180' |
| H | + | 14 | 0.2 | + | 0.2 | 150' |
| H | + | 15 | 0.04 | + | 0.04 | 360' |
| H | + | 10 | 0.04 | + | 0.04 | 150' |
| H | + | 2 | 0.04 | + | 0.04 | 150' |

TABLE-continued

| Active compounds ( ) identifying letter | or | Synergistic agents ( ) Compound No. | Concentration in % | LT 100 or % after 360 minutes |
|---|---|---|---|---|
| K | + | Piperonylbutoxide | 0.04 + 0.04 | 360' = 95% |
| K | + | 15 | 0.04 + 0.04 | 150' |
| L | + | 1 | 0.008 + 0.008 | 240' |
| L | + | 10 | 0.008 + 0.008 | 240' |
| L | + | 2 | 0.008 + 0.008 | 360' |
| M | + | Piperonylbutoxide | 0.04 + 0.04 | 360' |
| M | + | 1 | 0.04 + 0.04 | 150' |
| M | + | 13 | 0.04 + 0.04 | 150' |
| M | + | 14 | 0.04 + 0.04 | 150' |
| M | + | 15 | 0.04 + 0.04 | 150' |
| M | + | 10 | 0.04 + 0.04 | 60' |
| M | + | 2 | 0.04 + 0.04 | 60' |
| N | + | 1 | 0.008 + 0.008 | 120' |
| N | + | 13 | 0.008 + 0.008 | 150' |
| N | + | 14 | 0.008 + 0.008 | 150' |
| N | + | 15 | 0.008 + 0.008 | 210' |
| N | + | 2 | 0.008 + 0.008 | 105' |
| O | + | Piperonylbutoxide | 0.04 + 0.04 | 90' |
| O | + | 1 | 0.04 + 0.04 | 45' |
| O | + | 10 | 0.04 + 0.04 | 45' |
| O | + | 2 | 0.04 + 0.04 | 45' |
| P | + | Piperonylbutoxide | 0.2 + 0.2 | 360' = 50% |
| P | + | 1 | 0.2 + 0.2 | 150' |
| P | + | 12 | 0.2 + 0.2 | 240' |
| P | + | 13 | 0.2 + 0.2 | 240' |
| P | + | 14 | 0.2 + 0.2 | 180' |
| P | + | 15 | 0.2 + 0.2 | 210' |
| P | + | 10 | 0.2 + 0.2 | 360' = 90% |
| P | + | 2 | 0.2 + 0.2 | 360' = 95% |
| P | + | 6 | 0.2 + 0.2 | 360' = 90% |
| Q | + | Piperonylbutoxide | 0.04 + 0.04 | 360' = 90% |
| Q | + | 1 | 0.04 + 0.04 | 240' |
| Q | + | 12 | 0.04 + 0.04 | 210' |
| Q | + | 13 | 0.04 + 0.04 | 240' |
| Q | + | 14 | 0.04 + 0.04 | 180' |
| Q | + | 15 | 0.04 + 0.04 | 180' |
| R | + | Piperonylbutoxide | 1.0 + 1.0 | 360' = 20% |
| R | + | 1 | 0.2 + 0.2 | 120' |
| R | + | 10 | 0.2 + 0.2 | 360' = 95% |
| R | + | 2 | 0.2 + 0.2 | 180' |
| S | + | Piperonylbutoxide | 0.2 + 0.2 | 360' = 70% |
| S | + | 1 | 0.2 + 0.2 | 75' |
| S | + | 10 | 0.2 + 0.2 | 210' |
| S | + | 2 | 0.2 + 0.2 | 105' |
| U | + | Piperonylbutoxide | 0.008 + 0.008 | 210' |
| U | + | 1 | 0.008 + 0.008 | 120' |
| U | + | 13 | 0.008 + 0.008 | 75' |
| U | + | 15 | 0.008 + 0.008 | 180' |
| U | + | 10 | 0.008 + 0.008 | 120' |
| V | + | Piperonylbutoxide | 0.04 + 0.04 | 360' = 60% |
| V | + | 1 | 0.04 + 0.04 | 210' |
| V | + | 10 | 0.04 + 0.04 | 150' |
| V | + | 2 | 0.04 + 0.04 | 240' |
| W | + | Piperonylbutoxide | 0.2 + 0.2 | 360' = 95% |
| W | + | 1 | 0.2 + 0.2 | 210' |
| X | + | Piperonylbutoxide | 1.0 + 1.0 | 360' = 90% |
| X | + | 1 | 1.0 + 1.0 | 180' |
| X | + | 10 | 1.0 + 1.0 | 210' |
| X | + | 2 | 1.0 + 1.0 | 210' |
| Y | + | Piperonylbutoxide | 0.2 + 0.2 | 360' = 20% |
| Y | + | 1 | 0.2 + 0.2 | 360' |
| Z | + | Piperonylbutoxide | 1.0 + 1.0 | 360' = 45% |
| Z | + | 1 | 0.2 + 0.2 | 360' |
| Z | + | 2 | 0.2 + 0.2 | 360' |

It will be appreciated that the instant specification and examples are set forth by way of illustration and not limitation, and that various modifications and changes may be made without departing from the spirit and scope of the present invention.

What is claimed is:

1. A 3,5-dihalogeno-1,2-methylenedioxybenzene of the formula

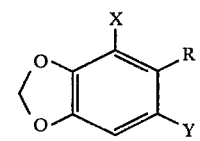

in which

R is hydrogen, cyano or an optionally substituted alkyl, alkenyl, alkynyl, aralkyl or acyl radical, the optional substituents being selected from the group consisting of chlorine or alkanoyl or alkanoyloxy each with up to 4 carbon atoms, but X and Y are not both bromine if R is hydrogen or unsubstituted alkyl, and X and Y each independently is halogen.

2. A compound of the formula

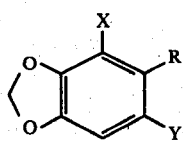

in which

R is hydrogen, alkyl, alkenyl or alkynyl of of up 4 carbon atoms, optionally substituted with chlorine, or alkanoyl or alkanoyloxy each with up to 4 carbon atoms, phenethyl, cyano or a radical of the formula

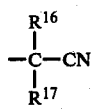

wherein $R^{16}$ is hydrogen or methyl, $R^{17}$ is hydrogen, alkyl with 1 to 5 carbon atoms, allyl, propargyl or benzyl, and X and Y each independently is fluorine, chlorine, bromine or iodine, but X and Y are not both bromine if R is hydrogen or unsubstituted alkyl.

3. A compound according to claim 1 wherein such compound is 3,5-dichloro-1,2-methylenedioxybenzene of the formula

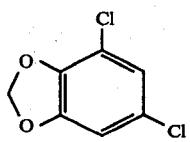

4. A compound according to claim 1 wherein such compound is 5-bromo-3-chloro-1,2-methylenedioxybenzene of the formula

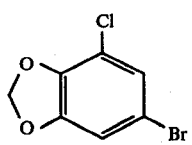

5. A compound according to claim 1 wherein such compound is 3,5-dichloro-4-methyl-1,2-methylenedioxybenzene of the formula

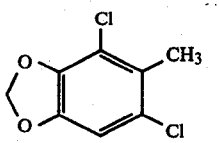

6. An arthopodicidal composition containing as active ingredients (1) at least one compound of the formula

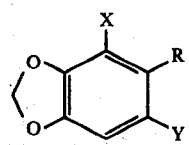

in which

R is hydrogen, halogen, cyano or an optionally substituted alkyl, alkenyl, alkynyl, aralkyl or acyl radical, the optional substituents being selected from the group consisting of chlorine or alkanoyl or alkanoyloxy each with up to 4 carbon atoms, and X and Y each independently is halogen but X and Y are not both bromine if R is hydrogen or unsubstituted alkyl, and (2) an arthropodicidally effective amount of at least one compound selected from the group consisting of (A) carbamates, (B) carboxylic acid esters (C) phosphoric acid exters and (D) halogenoalkanes.

7. A composition according to claim 6, wherein the weight ratio of component (1) to component (2) is from about 0.1:10 to 10 to 0.1.

8. A method of combating arthropods which comprises applying to the arthropods, or to a habitat thereof, an arthropodicidally effective amount of a composition according to claim 6.

9. The method according to claim 8, wherein component (1) is 3,5-dichloro-1,2-methylenedioxybenzene, or 3,5-dichloro-4-methyl-1,2-methylenedioxybenzene.

10. A compound according to claim 2, wherein such compound is 3,5-dichloro-4-cyanomethyl-1,2-methylenedioxybenzene of the formula

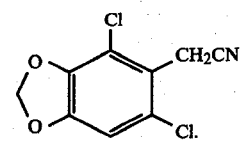

11. A compound according to claim 2, wherein such compound is 3,5-dichloro-4-α-cyanoethyl-1,2-methylenedioxybenzene of the formula

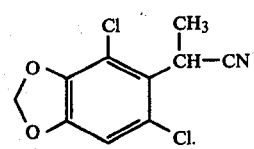

12. A compound according to claim 2, wherein such compound is 3,5-dichloro-4-α-cyanopropyl-1,2-methylenedioxybenzene of the formula

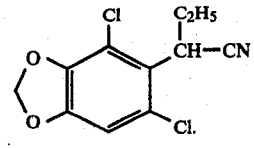

13. A compound according to claim 2, wherein such compound is 3,5-dichloro-4-(1-cyano-2-methyl-propyl)-1,2-methylenedioxybenzene of the formula

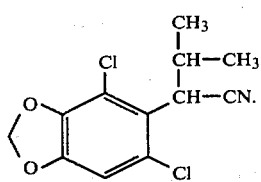

14. An arthropodicidal composition containing as active ingredients (1) at least one compound of the formula

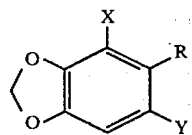

in which

R is hydrogen, alkyl, alkenyl or alkynyl of up to 4 carbon atoms, optionally substituted with chlorine, or alkanoyl or alkanoyloxy each with up to 4 carbon atoms, phenethyl, cyano or a radical of the formula

wherein
$R^{16}$ is hydrogen or methyl,
$R^{17}$ is hydrogen, alkyl with 1 to 5 carbon atoms, allyl, propargyl or benzyl, and
X and Y each independently is fluorine, chlorine, bromine or iodine, but X and Y are not both bromine if R is hydrogen or unsubstituted alkyl, and
(2) an arthropodicidally effective amount of at least one compound selected from the group consisting of (A) carbamates, (B) carboxylic acid esters (C) phosphoric acid esters and (D) halogenoalkanes.

15. A composition according to claim 14, wherein the weight ratio of component (1) to component (2) is from about 0.1:10 to 10:0.1.

16. A method of combating arthropods which comprises applying to the arthropods, or to a habitat thereof, an arthropodicidally effective amount of a composition according to claim 2.

17. The method according to claim 14, wherein component (1) is
3,5-dichloro-4-cyanomethyl-1,2-methylenedioxybenzene,
3,5-dichloro-4-α-cyanoethyl-1,2-methylenedioxybenzene,
3,5-dichloro-4-α-cyanopropyl-1,2-methylenedioxybenzene or
3,5-dichloro-4-(1-cyano-2-methyl-propyl)-1,2-methylenedioxybenzene.

* * * * *